United States Patent
Mostapha et al.

(10) Patent No.: US 12,008,690 B2
(45) Date of Patent: Jun. 11, 2024

(54) ITERATIVE HIERARCHAL NETWORK FOR REGULATING MEDICAL IMAGE RECONSTRUCTION

(71) Applicant: Siemens Healthcare GmbH, Erlangen (DE)

(72) Inventors: Mahmoud Mostapha, Princeton, NJ (US); Boris Mailhe, Plainsboro, NJ (US); Mariappan S. Nadar, Plainsboro, NJ (US); Simon Arberet, Princeton, NJ (US); Marcel Dominik Nickel, Herzogenaurach (DE)

(73) Assignee: Siemens Healthineers AG, Forchheim (DE)

( * ) Notice: Subject to any disclaimer, the term of this patent is extended or adjusted under 35 U.S.C. 154(b) by 609 days.

(21) Appl. No.: 17/155,630

(22) Filed: Jan. 22, 2021

(65) Prior Publication Data
US 2022/0165002 A1  May 26, 2022

Related U.S. Application Data

(60) Provisional application No. 63/118,115, filed on Nov. 25, 2020.

(51) Int. Cl.
| | |
|---|---|
| *G06K 9/00* | (2022.01) |
| *G06N 3/04* | (2023.01) |
| *G06N 3/08* | (2023.01) |
| *G06T 11/00* | (2006.01) |
| *G16H 30/20* | (2018.01) |
| *G16H 30/40* | (2018.01) |

(52) U.S. Cl.
CPC .............. *G06T 11/008* (2013.01); *G06N 3/04* (2013.01); *G06N 3/08* (2013.01); *G06T 11/006* (2013.01); *G16H 30/20* (2018.01); *G16H 30/40* (2018.01); *G06T 2210/41* (2013.01); *G06T 2211/424* (2013.01)

(58) Field of Classification Search
CPC . G06T 11/008; G06T 11/006; G06T 2210/41; G06T 2210/424; G16H 30/20; G16H 30/40; G06N 3/04; G06N 3/08
See application file for complete search history.

(56) References Cited

U.S. PATENT DOCUMENTS

| | | | |
|---|---|---|---|
| 10,499,069 B2 * | 12/2019 | Wang | G06T 5/002 |
| 10,527,699 B1 * | 1/2020 | Cheng | G06N 3/088 |
| 10,712,416 B1 * | 7/2020 | Sandino | G06N 3/045 |

(Continued)

OTHER PUBLICATIONS

Chen et al. "Automatic fetal ultrasound standard plane detection using knowledge transferred recurrent neural networks." Medical Image Computing and Computer-Assisted Intervention-MICCAI 2015, Springer International Publishing, 2015 (Year: 2015).*

(Continued)

*Primary Examiner* — Duy M Dang (57) ABSTRACT

For reconstruction in medical imaging, such as reconstruction in MR imaging, an iterative, hierarchal network for regularization may decrease computational complexity. The machine-learned network of the regularizer is unrolled or made iterative. For each iteration, nested U-blocks form a hierarchy so that some of the down-sampling and up-sampling of some U-blocks begin and end with lower resolution data or features, reducing computational complexity.

20 Claims, 5 Drawing Sheets

(56) References Cited

U.S. PATENT DOCUMENTS

| | | | |
|---|---|---|---|
| 2018/0285695 A1* | 10/2018 | Guo | G06T 11/008 |
| 2019/0369190 A1* | 12/2019 | Ye | G06N 3/08 |
| 2020/0011951 A1* | 1/2020 | Shi | G01R 33/56536 |
| 2020/0103483 A1* | 4/2020 | Hardy | G01R 33/5608 |
| 2020/0294282 A1* | 9/2020 | Schlemper | G06N 3/088 |
| 2020/0408864 A1 | 12/2020 | Mailhe | |
| 2021/0035339 A1* | 2/2021 | Ahn | G06N 3/084 |
| 2021/0118200 A1* | 4/2021 | Akcakaya | G06N 3/04 |
| 2021/0201499 A1* | 7/2021 | Qin | G06T 7/143 |
| 2021/0208227 A1* | 7/2021 | Hardy | G01R 33/56545 |
| 2021/0217213 A1* | 7/2021 | Cole | G06N 3/088 |
| 2022/0373631 A1* | 11/2022 | Correia | G01R 33/561 |

OTHER PUBLICATIONS

Adler, Jonas, and Ozan Öktem. "Learned primal-dual reconstruction." IEEE transactions on medical imaging 37.6 (2018): 1322-1332 (Year: 2018).*

Liang, Dong, et al. "Deep MRI reconstruction: unrolled optimization algorithms meet neural networks." arXiv preprint arXiv: 1907.11711 (2019) (Year: 2019).*

Du, Jinglong, et al. "Accelerated super-resolution MR image reconstruction via a 3D densely connected deep convolutional neural network." 2018 IEEE international conference on bioinformatics and biomedicine (BIBM). IEEE, 2018. (Year: 2018).*

Cheng, Jing, et al. "Model-based deep medical imaging: the roadmap of generalizing iterative reconstruction model using deep learning." arXiv preprint arXiv:1906.08143 (2019). (Year: 2019).*

Liang, Dong, et al. "Deep magnetic resonance image reconstruction: Inverse problems meet neural networks." IEEE Signal Processing Magazine 37.1 (2020): 141-151. (Year: 2020).*

Knoll, Florian, et al. "Deep learning methods for parallel magnetic resonance image reconstruction." arXiv preprint arXiv:1904.01112 (2019). (Year: 2019).*

Cheng, Jing, et al. "Model learning: Primal dual networks for fast MR imaging." Medical Image Computing and Computer Assisted Intervention-MICCAI 2019: 22nd International Conference, Shenzhen, China, Oct. 13-17, 2019, Proceedings, Part III 22. Springer International Publishing, 2019. (Year: 2019).*

Qin, Chen, et al. "Convolutional recurrent neural networks for dynamic MR image reconstruction." IEEE transactions on medical imaging 38.1 (2018): 280-290. (Year: 2018).*

Pezzotti, Nicola, et al. "An adaptive intelligence algorithm for undersampled knee MRI reconstruction." IEEE Access 8 (2020):204825-204838. (Year: 2020).*

Ke, Ziwen, et al. "CRDN: cascaded residual dense networks for dynamic MR imaging with edge-enhanced loss constraint." arXiv preprint arXiv:1901.06111 (2019). (Year: 2019).*

Sriram, Anuroop, et al. "End-to-End Variational Networks for Accelerated MRI Reconstruction." arXiv preprint arXiv:2004.06688 (2020).

U.S. Appl. No. 16/688,170 filed Nov. 19, 2019.
U.S. Appl. No. 17/097,060, filed Nov. 13, 2020.

* cited by examiner

ITERATIVE HIERARCHAL NETWORK FOR REGULATING MEDICAL IMAGE RECONSTRUCTION

RELATED APPLICATIONS

The present patent document claims the benefit of the filing date under 35 U.S.C. § 119(e) of Provisional U.S. Patent Application Ser. No. 63/118,115, filed Nov. 25, 2020, which is hereby incorporated by reference.

FIELD

This disclosure relates to medical image reconstruction, such as reconstruction in magnetic resonance (MR) imaging.

BACKGROUND

Medical imaging, such as magnetic resonance (MR), computed tomography (CT), positron emission tomography (PET), or single photon emission computed tomography (SPECT), use reconstruction to estimate an image or real-space object from measurements. These scans may be time consuming. For example, numerous methods have been proposed to accelerate the MR scan. One acceleration method is the under-sampling reconstruction technique (i.e., MR parallel imaging with compressed sensing (CS)), where fewer samples are acquired in the MRI data space (k-space), and prior knowledge is used to restore the images in reconstruction. MR results obtained using compressed sensing reconstruction tend to show unfolding artifacts. An image regularizer is used in reconstruction to reduce these aliasing artifacts, but the regularizer adds computational burden.

Deep learning (DL) techniques based on unfolding (unrolled) iterative reconstruction algorithms with learnable regularization improve the speed and the reconstruction quality compared to CS. Some DL-based image reconstruction methods are based on unrolled iterative algorithms where a data-consistency step alternates with a regularization network. In order to obtain good results, multiple unrolled iterations of reconstruction are performed. Computational time and memory requirements are directly proportional to the number of unrolled iterations. Deep learning models need to be fast and memory-efficient while also robust to variations in MRI intensities and contrasts originating from using different scanned organs, acquisition parameters, and image resolutions. Current MRI reconstruction schemes typically utilize image regularization deep learning networks in the form of an encoding-decoding structure such as different U-net architectures. Decreasing and increasing the resolution of the feature maps is effective for learning from heterogeneous datasets, but U-net architectures increase the overall size of the feature maps, resulting in decreasing the receptive field and increasing the computational complexity.

SUMMARY

By way of introduction, the preferred embodiments described below include methods, systems, instructions, and computer readable media for reconstruction in medical imaging, such as reconstruction in MR imaging. In reconstruction, an iterative, hierarchal network for the regularization may decrease computational complexity. The machine-learned network of the regularizer is unrolled or made iterative. For each iteration, nested U-blocks form a hierarchy so that some of the down-sampling and up-sampling of some U-blocks begin and end with lower resolution data or features, reducing computational complexity.

In a first aspect, a method is provided for reconstruction of a medical image in an medical imaging system. The medical imaging system scans a patient, resulting in measurements. An image processor reconstructs the medical image from the measurements. The reconstruction includes a regularizer implemented with a machine-learned network comprising a hierarchy of iterative convolutional networks, each of the iterative convolutional networks including both down-sampling and up-sampling. The medical image is displayed.

In one embodiment, the medical imaging system is a magnetic resonance (MR) scanner, and the measurements are k-space measurements. In another embodiment, a complex image is output by a gradient update in the reconstruction. The machine-learned network has a two-channel input for the complex image and outputs the medical image with complex values.

Various reconstruction algorithms may be used. In one embodiment, an unrolled iterative reconstruction is performed where each of multiple reconstructions in the unrolled iterative reconstruction includes regularization. The regularizer provides the regularization for at least one of the multiple reconstructions.

Various network architectures may be used for the machine-learned network and/or the iterative hierarchal convolution networks of the machine-learned network used in regularizing for reconstruction. In one embodiment, the machine-learned network includes a feature extraction block including one or more convolution layers. The feature extraction block is prior to the hierarchy of iterative convolutional networks. In another embodiment, the iterative hierarchal convolutional networks have different weights. In a further embodiment, the machine-learned network further includes a memory network with convolution layers where the memory network is applied separately to the outputs of the iterative convolutional networks. The machine-learned network may further include an enhancement block of one or more convolutional layers. The enhancement block receives a concatenation of outputs of the memory network and outputs the medical image as regularized. In yet another embodiment, the iterative convolutional networks each include U-blocks at different levels of the down-sampling and the up-sampling and at least one concatenation connection in parallel with a bottleneck. The U-blocks may themselves include down-sampling and up-sampling layers and have local and global connections.

The machine-learned network for regularization in reconstruction may be trained for use in multiple applications. For example, the scanning is for patient diagnosis with one of different imaging applications for different anatomy and/or disease. The machine-learned network is applied independent of the different imaging applications. This broad application allows the machine-learned network to have been trained on reconstructions for the different imaging applications, increasing the available training data.

In a second aspect, a method is provided of machine training for reconstruction in medical imaging. A neural network with an unrolled arrangement of U-blocks in a sequence is machine trained as a regularizer for the reconstruction in the medical imaging. The neural network as machine trained is stored.

In one embodiment, the U-blocks of the neural network being trained are convolutional neural networks with down-sampling and up-sampling. In another embodiment, each of the U-blocks in the sequence has a hierarchy of U-networks.

In a further embodiment, each of the U-networks in the hierarchy has local and global residual connections.

The neural network may have other structure for training. For example, the neural network further includes a convolution network configured to receive outputs from the U-blocks of the sequence and separately process the outputs with shared weights.

The neural network for regularization may be trained to operate in various imaging applications. The machine training uses ground truth imaging from different medical applications and/or types of imaging.

In a third aspect, a system is provided for reconstruction in medical imaging. A medical scanner is configured to scan a region of a patient. The scan provides scan data. An image processor is configured to reconstruct a representation of the region from the scan data. The image processor is configured to reconstruct by application of a machine-learned model in a regularization stage. The machine-learned model includes a down-sampling and up-sampling first block having multiple down-sampling and up-sampling second blocks. A display is configured to display an image of the region from the reconstructed representation.

In one embodiment, the down-sampling and up-sampling first block is one of a sequence of down-sampling and up-sampling first blocks in the regularization stage. In another embodiment, the down-sampling and up-sampling first block is a first convolutional neural network, and the down-sampling and up-sampling second blocks are second convolutional neural networks.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

An image regularization network has a hierarchical design that iteratively down-samples the input image feature maps followed by an up-sampling procedure. This deep iterative hierarchical network (DIHN) has improved memory efficiency, such as using 20-30% less GPU memory, compared to conventional U-Net architectures in the regularizer. The improved memory efficiency results, at least in part, from the DIHN performing most of the computations on a coarser scale due to the hierarchy. Moving the computation to a coarser scale does not limit analysis at the finest scale due to the hierarchical design, allowing DIHN to regulate reconstruction models when learning from heterogeneous MRI datasets. This more efficient regularization in reconstruction is capable of processing a wide range of imaging variability with a single model without requiring explicit meta-data inputs. As a result, images from different imaging applications (i.e., different settings) and/or types of imaging may be used to train the model, providing a larger training dataset. The one trained model may then be used for any of the various imaging applications and/or types of imaging without requiring multiple application or type-specific models.

Figure 1:
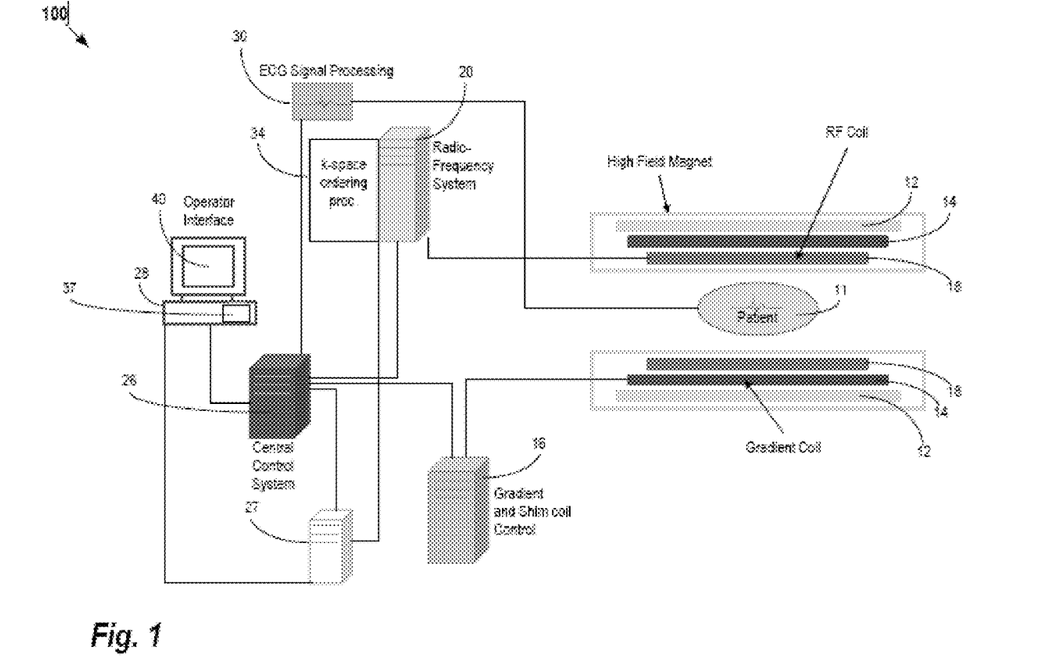
FIG. 1 is a block diagram of an embodiment of an MR system for medical imaging using an iterative and/or hierarchal network for regulating.

FIG. 1 shows one embodiment of a system for reconstruction in medical imaging. An image regularization network has a hierarchical design that iteratively down-samples the input image feature maps followed by an up-sampling procedure.

The example used herein is in a magnetic resonance context (i.e., a magnetic resonance scanner), but the iterative and/or hierarchal regularizer network may be used in reconstruction for CT, PET, SPECT, or other medical imaging. The iterative and/or hierarchal regularizer network is used for reconstruction into an object or image domain from projections or measurements in another domain. In the discussion below, the MR context is used.

The system uses a machine-learned model in reconstruction. The machine-learned model is formed from one or more networks and/or another machine-learned architecture. For example, the machine-learned model is a deep learned neural network. The machine-learned model is used for regularization of reconstruction. Image or object domain data is input, and image or object domain data with less artifact is output. The machine-learned model assists in compressed, parallel sensing, or other MR imaging for more rapid scanning and less computational burden in reconstruction. The remaining portions or stages of the reconstruction (e.g., Fourier transform and gradients in iterative optimization) are performed using reconstruction algorithms and/or other machine-learned networks.

The system is implemented by an MR scanner or system, a computer based on data obtained by MR scanning, a server, or another processor. MR scanning system 100 is only exemplary, and a variety of MR scanning systems can be used to collect the MR data. In the embodiment of FIG. 1, the system is or includes the MR scanner or MR system 100. The MR scanner 100 is configured to scan a patient. The scan provides scan data in a scan domain. The system 100 scans a patient to provide k-space measurements (measurements in the frequency domain). In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field, and a readout gradient magnetic field that are applied to patient 11.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image (i.e., for reconstruction in the object domain from the k-space data in the scan domain). In some embodiments, the image data processor is located in or is the central control unit 26. In other embodiments, such as the one depicted in FIG. 1, the image data processor is located in a separate unit 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized. The central control processor 26 is programmed to sample the MR signals according to a predetermined sampling pattern. Any MR scan sequence may be used, such as for T1, T2, or other MR parameter. In one embodiment, a compressive sensing scan sequence is used.

The central control unit 26 also uses information stored in an internal database to process the detected MR signals in a coordinated manner to generate high quality images of a selected slice(s) of the body (e.g., using the image data processor) and adjusts other parameters of system 100. The stored information includes a predetermined pulse sequence and a magnetic field gradient and strength data as well as data indicating timing, orientation and spatial volume of gradient magnetic fields to be applied in imaging.

The central control unit 26 (i.e., controller) and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used.

The image processor is configured by software, firmware, or hardware to reconstruct. The image processor operates pursuant to stored instructions on a non-transitory medium to perform various acts described herein.

The image processor is configured to reconstruct a representation in an object domain. The object domain is an image space and corresponds to the spatial distribution of the patient. A planar area or volume representation is reconstructed as an image representing the patient. For example, pixels values representing tissue in an area or voxel values representing tissue distributed in a volume are generated.

The representation in the object domain is reconstructed from the scan data in the scan domain. The scan data is a set or frame of k-space data from a scan of the patient. The k-space measurements resulting from the scan sequence are transformed from the frequency domain to the spatial domain in reconstruction. In general, reconstruction is an iterative process, such as a minimization problem. This minimization can be expressed as:

$$x = \underset{x}{\operatorname{argmin}} \|Ax - y\|_2^2 + \lambda \|Tx\|_1 \tag{1}$$

where x is the target image to be reconstructed, and y is the raw k-space data. A is the MRI model to connect the image to MRI-space (k-space), which can involve a combination of an under-sampling matrix U, a Fourier transform F, and sensitivity maps S. T represents a sparsifying (shrinkage) transform. $\lambda$ is a regularization parameter. The first term of the right side of equation 1 represents the image (2D or 3D spatial distribution or representation) fit to the acquired data, and the second term of the right side is a term added for denoising by reduction of artifacts (e.g., aliasing) due to under sampling. The l1 norm is used to enforce sparsity in the transform domain. $\|Ax-y\|_2^2$ is the l2 norm of the variation of the under-sampled k-space data. Generally, the lp norm is $\sqrt[p]{\Sigma|x|^p}$. In some embodiments, the operator T is a wavelet transform. In other embodiments, the operator T is a finite difference operator in the case of Total Variation regularization.

Figure 2:
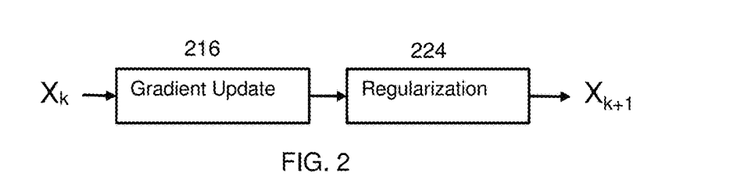
FIG. 2 shows an embodiment of iteration in reconstruction.

The reconstruction is iterative, such as repeating the reconstruction operation to minimize. In some embodiments, an unrolled iterative reconstruction is provided as a network or model of iteration sequences. As shown in FIG. 2, a given iteration either in an unrolled network or through a repetition of the reconstruction operations includes a gradient update 216 (e.g., first term of equation 1) and regularization 224 (e.g., second term of equation 1). The gradient update 216 compares the current image object with the scan data (e.g., k-space measurements, y). This comparison uses a system transform to relate the measurements to the image object. Any gradient or comparison relating the image object to the measurements may be used. As shown in FIGS. 2, the regularization 224 operates on the output of the gradient update 216. The regularizer is, at least in part, a machine-learned network. A machine-learned model is applied in the regularization stage. In one embodiment, deep learning is used to train a convolutional neural network (CNN) as the regularizer. Regularization may not be included in all the iterations. Input bias field correction and/or extrapolation for momentum may be provided as part of the reconstruction. Other filtering and/or operations for reconstruction and/or post-reconstruction may be provided.

The regularizer 224 is implemented as a machine-learned model, such as a machine-learned network. Machine learning is an offline training phase where the goal is to identify an optimal set of values of learnable parameters of the model that can be applied to many different inputs (i.e., image domain data after gradient calculation in the optimization or minimization of the reconstruction). These machine-learned parameters can subsequently be used during clinical operation to rapidly regularize the reconstruction of images. Once learned, the machine-learned model is used in an online processing phase in which images from the gradient update 216 is input and the regularized image for the patients are output based on the model values learned during the training phase.

During application to one or more different patients and corresponding different scan data, the same learned weights or values for the regularization 224 are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The model has an architecture. This structure defines the learnable variables and the relationships between the variables. In one embodiment for the regularization 224, a neural network is used, but other networks or machine learning models may be used. In one embodiment, a convolutional neural network (CNN) is used. Any number of layers and nodes within layers may be used. A DenseNet, U-Net, encoder-decoder, Deep Iterative Down-Up CNN, and/or another network may be used. Some of the network may include dense blocks (i.e., multiple layers in sequence outputting to the next layer as well as the final layer in the dense block). Any know known or later developed neural network may be used.

The image processor is configured to reconstruct with the machine-learned model (e.g., CNN) trained as a regularizer in the reconstruction. The iterative reconstruction may be unrolled where a given number of iterations of gradient update 216 and regularization 224 is used. The same CNN is used for each iteration. Alternatively, a different CNN is provided for each iteration, whether a different architecture or same architecture but with different values for one or more of the learnable parameters of the CNN. Different CNNs are trained for different iterations in the reconstruction. Each CNN may have the same architecture, but each is separately learned so that different values of the learnable parameters may be provided for different iterations of the reconstruction.

The machine-learned model forming the regularizer 224 is hierarchal and/or iterative. As hierarchal, the model includes down and up-sampling where additional networks of down and up-sampling are provided as layers or blocks within the down and up-sampling (i.e., nested U-blocks). For example, a given top level architecture includes down and up-sampling, and a block after an initial down-sampling and before a final up-sampling includes a lower level architecture that also includes both down and up-sampling. Multiple blocks at the same or different levels or scales of the top-level architecture may include down and up-sampling.

As iterative, the model includes multiple networks in sequence. An unrolled architecture is provided where the same or different network architecture is provided for each of multiple iterations feeding forward through the iterations to output a final regularized image object for the given reconstruction iteration. Where the reconstruction is unrolled, the iteration in the regularizer is an iteration within the one of the reconstruction iterations. Each or some of the reconstruction iterations may include iterative regularization.

The model for regularization may be both iterative and hierarchal. For example, an unrolled sequence of CNNs are provided for regularization. Each of the CNNs include nested or hierarchal down and up-sampling blocks implemented as CNNs, resulting in down and up-sampling of features at lower resolutions within the CNN that is also down and up-sampling at a top level.

Figure 3:
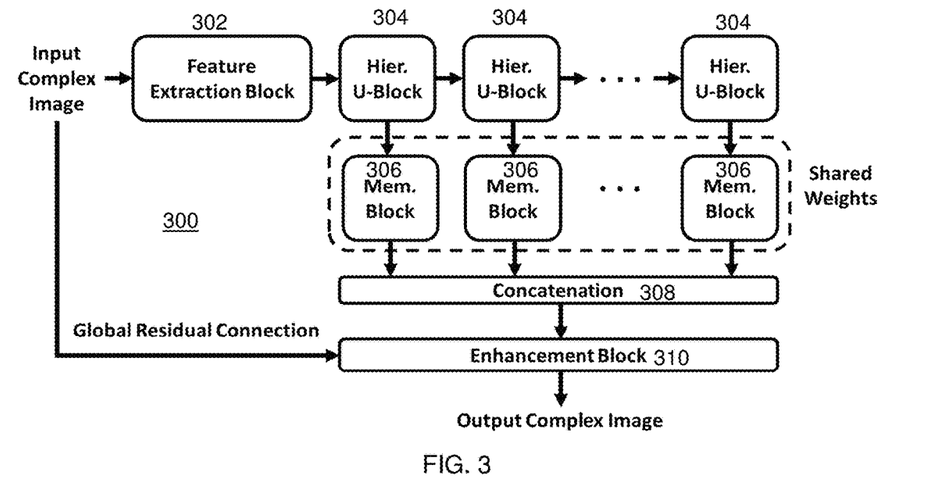
FIG. 3 is a block diagram of one embodiment of an iterative network for regulating in a given iteration of reconstruction.
Figure 4:
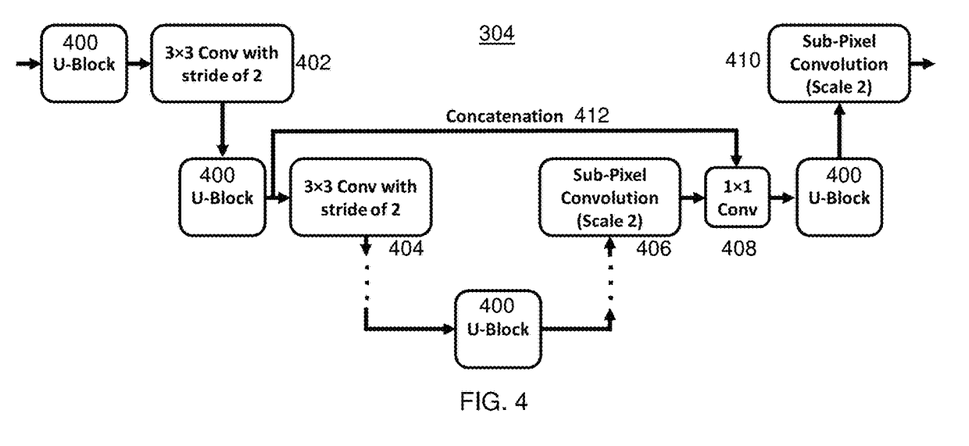
FIG. 4 is a block diagram of one embodiment of a hierarchal U-block network for regulating.
Figure 5:
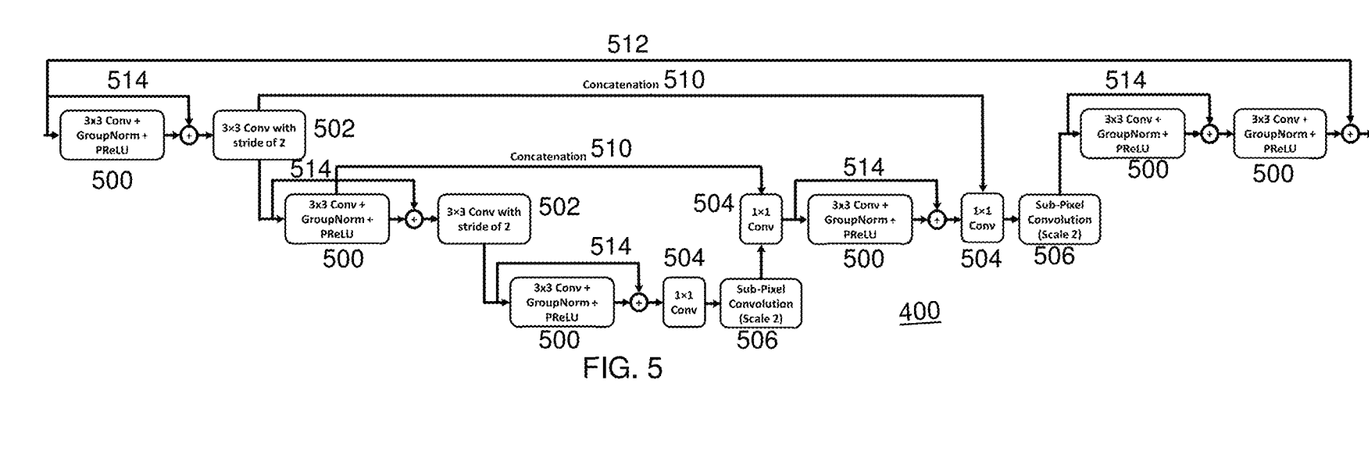
FIG. 5 is a block diagram of one embodiment of a U-block architecture used in a hierarchal U-block network.

FIGS. 3-5 show an example CNN architecture for an iterative hierarchal model or network. The reconstruction includes the regularizer model 300, implemented at least in part as a machine-trained model. The input is an image from the gradient update 216. In this example, the image is in the object domain and represented as complex data (i.e., real and imaginary). In other embodiments, such as using Dixon scan for MR, the input data is real, not complex. The regularizer model 300 receives the data (e.g., complex image or object data) output by the gradient update 216.

The model 300 includes an optional feature extraction block 302. The feature extraction block 302 receives the input image and outputs to the iterative portion (i.e., blocks 304) of the model 300. The feature extraction block 302 is a neural network, such as a CNN implementing a one or more convolution layers to increase the number of feature maps. For example, two input channels are increased to thirty-two output channels. As another example, the input complex image is first passed through the initial feature extraction block 302 where twice the number of input feature maps are extracted with half the image resolution achieved through convolutions with stride 2. The feature extraction block 302 down samples without up-sampling (e.g., by stride 2). No or greater down-sampling (e.g., stride 4) may be used. The down-sampling reduces the amount of data as compared to no down-sampling. Dilated convolution may be used to maintain the depth and computational complexity of the network while increasing the receptive field. Dilated convolution may not be used to avoid gridding artifact as features are sparsely down-sampled.

The model 300 includes iterative regularization. A series of hierarchal or non-hierarchal U-blocks 304 are provided. Hierarchal is used in the example embodiment of FIG. 3. Each hierarchal U-block 304 is a convolution neural network. The initial hierarchal U-block 304 receives the complex image, features output by the feature extraction block 302, and/or a combination thereof as input. The initial hierarchal U-block 304 outputs to the next hierarchal U-block 304 in the unrolled series and outputs to a memory block 306. Each successive hierarchal U-block 304 receives input from the previous hierarchal U-block 304 and outputs to the next hierarchal U-block 304 and the memory block 306. The last hierarchal U-block 304 of the series outputs to the memory block 306. Any number of hierarchal U-blocks 304 may be provided, such as two, three, four, eight, twelve, or sixteen.

In training, each hierarchal U-block 304 is a separate network with the same architecture. As a result, the same learnable parameter may have a different learned value for one hierarchal U-block 304 as compared to any others of the hierarchal U-blocks 304. In other embodiments, the architecture also varies so that different architectures are provided for different ones of the hierarchal U-blocks 304.

The hierarchal U-blocks 304 are hierarchal. In one embodiment, each of the iterative U-blocks 304 (e.g., CNNs) are hierarchal. One or more other blocks and/or iterative U-blocks 304, which are not hierarchal, may be provided.

FIGS. 4 and 5 show an example hierarchal U-block 304 implemented as a CNN. The hierarchal U-block 304 includes nested down-sampling and up-sampling. For example, FIG. 4 shows the hierarchal U-block 304 as including U-blocks 400, each of which also includes down-sampling followed by up-sampling. The result is a hierarchy of down and up-sampling at one or more resolution levels within down and up-sampling. The interior down and up-sampling blocks operate on reduced resolution data, so are less computationally and memory expensive.

The hierarchal U-block 304 of at least one iteration of regularization includes U-blocks 400. These U-blocks 400 are provided at different levels of the down and up-sampling of the hierarchal U-block 304. In the example architecture of FIG. 4, a U-block 400 receives the input. A 3×3 or other sized convolution layer 402 with a stride of 2 or other stride downs samples the output of the initial U-block 400. The convolution layer 402 outputs to another U-block 400, which outputs to another 3×3 or other sized convolution layer 404 with a stride of 2 or other stride and outputs to a concatenation 412. The convolution layer 404 down samples, and outputs to one or more additional layers or levels of U-blocks 400 and convolution layers for down sampling. The down sampling continues until the lowest level or resolution U-block 400 is reached at the bottleneck of the hierarchal U-block 304. Similarly, corresponding up-sampling provided by sub-pixel convolution layers 406, 410 with intervening U-blocks 400 is provided. A U-block 400 is not provided at the output but may be. While a scale of 2 is shown, other up-sampling scales may be used.

The concatenation may be a convolution layer or other structure. The concatenation generates additional features, providing more output features than input to the concatenation. In alternative embodiments, the number of features is not increased, a skip connection without any network layers, a residual connect layer (e.g., sum), or other operation is provided. While only one concatenation 412 is shown for one level or resolution (scale), other concatenations at other levels may be provided. The concatenation 412 is parallel with the bottleneck, skipping part of the network to pass between the down sampling chain and the up-sampling chain at a same resolution.

In this machine-learned model 300 of FIG. 3, the extracted features are passed through several hierarchal U-blocks 304 of FIG. 4. The hierarchal U-blocks 304 are composed of a several U-blocks 400 interspersed with down-sampling, allowing efficient processing at a coarser scale before up-sampling the processed feature maps using subpixel convolutions 406, 410. Each U-block 400 itself includes an architecture that has down-sampling, followed by up-sampling.

FIG. 5 shows an example CNN architecture for each U-block 400. All the U-blocks 400 may have the same or different architecture. The down-sampling chain includes layers 500 with convolution (e.g., 3×3), group normalization, and PReLU activation and down sampling convolution layers 502 with any stride (e.g., 2). The up-sampling chain after the bottle neck (i.e., lowest scale) includes layers 500 as well as 1×1 convolutions 504 and sup-pixel convolutions 506 with any scale (e.g., 2).

Group normalization is used, but batch or other normalization layers may be provided instead. PReLU activation is used to provide the network with additional modeling flexibility, but ReLU, leaky ReLU, or other activation functions may be used. Sub-pixel convolutions are used for upscaling the feature maps for computational efficiency, but transposed convolutions with the desired scale may alternatively be used to additionally increase the model flexibility.

The U-block 400 includes concatenation 510 at the different scales. A global connection 512 is included, so that the input is passed to the output. Local connections 514 connect inputs to outputs for the convolution layers 500. These local and global connections 512, 514 are skip connections passing the inputs to be summed with the outputs of the convolution layers 500 and the entire U-block 400, respectively. The local and global residual connections 512, 514 enhance information flow while maintaining efficient memory usage, such as compared to dense connections.

Other architectures for the U-block 400 may be used. Other hierarchal architectures for the hierarchal U-blocks 304 may be used. Other iterative architectures of the machine-learned model 300 for regularization may be used.

Returning to FIG. 3, the machine-learned model includes the memory block 306. The memory block 306 is formed from convolution layers, such as being a CNN. The memory block 306 does not but may include down-sampling and/or up-sampling. In one embodiment, the memory block 306 includes the architecture of the U-block 400 without the convolution layers 502 and without the convolution layers 506. Other architectures may be used.

FIG. 3 shows separate memory blocks 306 with shared weights. The same memory block 306 is applied separately to the outputs of the different hierarchal U-blocks 304. Alternatively, separate memory blocks 306 are trained for the separate or iterative hierarchal U-blocks 304. The memory block 306 is provided to combine the outputs of the hierarchical U-blocks 304. The memory block 306 may extract features from the output of the hierarchal U-blocks 304 and/or from different scales within the hierarchal U-blocks 304. The memory block 306 processes the extracted feature maps at different levels.

The machine-learned model 300 includes a concatenation 308. The concatenation 308 is a memory storing a collection of the features output by the memory block 306. The memory block 306 concatenates the memory block outputs before passing the features to the final enhancement block 310. The concatenation 308 is formed from neural network layers in other embodiments, such as providing further convolution layers.

The machine-learned model 300 includes an enhancement block 310. The enhancement block 310 is one or more convolution layers to refine the output. In one embodiment, 1×1 convolution is used to fuse the concatenated representations. Where the feature extraction block 302 includes down-sampling without a corresponding up-sampling, the enhancement block 310 includes a sub-pixel convolution layer to generate the final complex output image at the resolution or scale of the input to the machine-learned model 300. A global residual connection may input the input image to the enhancement block 310. The enhancement block 310 receives a concatenation 308 of outputs of the memory block 306 and the input image and outputs the medical image as regularized.

The output medical image is formed from complex values. Real values may be output in other embodiments.

The output complex image is the final reconstructed image if the regularization is the final iteration of the reconstruction. The output image represents the patient (i.e., a reconstructed representation). Otherwise, the output complex image is the image generated for a given reconstruction iteration. This image is then used in the next reconstruction iteration for the gradient update.

The image processor may be configured to generate an MR image from the reconstructed representation. Where the representation is of an area, the values of the representation may be mapped to display values (e.g., scalar values to display color values) and/or formatted (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

Generated images of the reconstructed representation for a given patient are presented on a display 40 of the operator interface. The computer 28 of the operator interface includes a graphical user interface (GUI) enabling user interaction with central control unit 26 and enables user modification of magnetic resonance imaging signals in substantially real time. The display processor 37 processes the magnetic resonance signals to provide image representative data for display on display 40, for example.

The display 40 is a CRT, LCD, plasma, projector, printer, or other display device. The display 40 is configured by loading an image to a display plane or buffer. The display 40 is configured to display the reconstructed MR image of a region of the patient.

Figure 6:
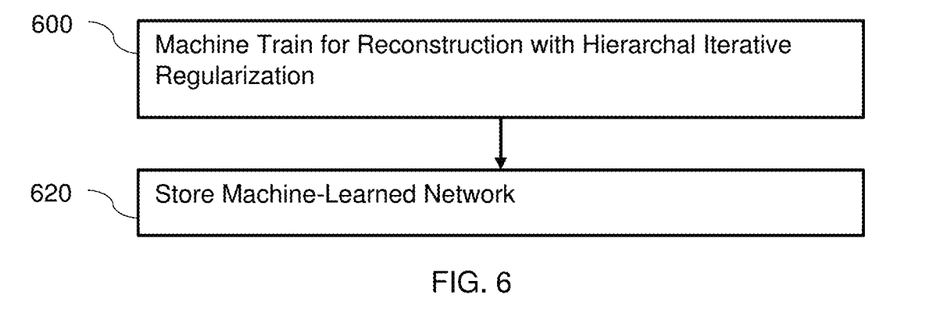
FIG. 6 is a flow chart diagram of one embodiment of a method for machine training for regularizing in reconstruction.

FIG. 6 is a flow chart diagram of one embodiment of a method for machine training for reconstruction in medical imaging, such as training a neural network to regularize in reconstruction from signals collected by an MR scanner. Once trained, the machine-learned model (e.g., regularization) may be used with the same learned values in reconstruction of representations for any number of patients from a respective number of sets of MR scan data for the patients.

The method is implemented by a computer, such as a personal computer, workstation, and/or server. Other computers may be configured to perform the acts of FIG. 6. The MR scanner 100 or central control unit 26 may implement the method. In one embodiment, the computer and a database are used to machine train and store the samples and the resulting final trained model. The stored model is then distributed to one or more MR scanners 100 for application using the model as fixed (i.e., the learned values of the variables are not changed for reconstructions for a given patient and/or for different patients).

Figure 7:
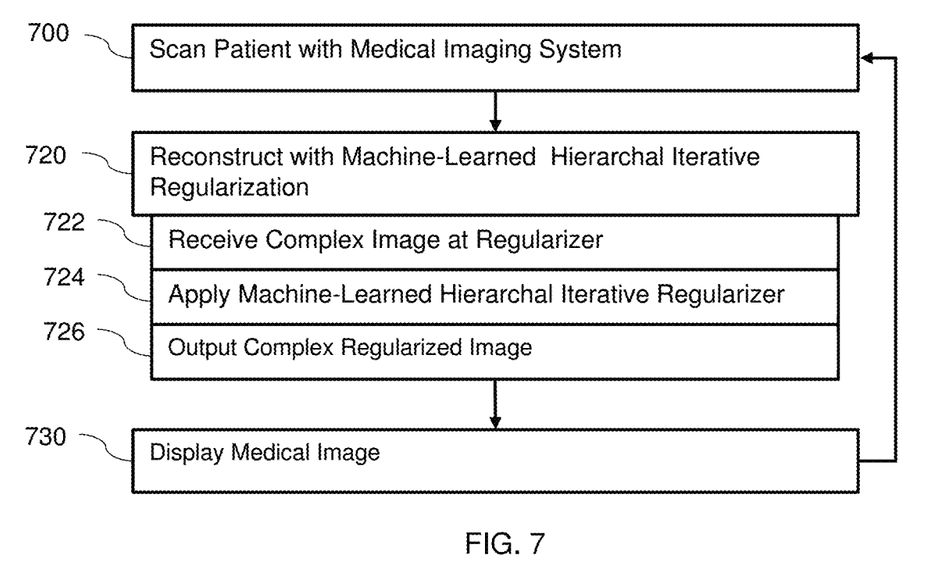
FIG. 7 is a flow chart diagram of one embodiment of a method for reconstruction using a machine-learned network for regularization.

The method is performed in the order shown (i.e., top to bottom or numerical). Additional, different, or fewer acts may be provided. For example, instead of or in addition to storing in act 620, the machine-learned model is applied to previously unseen scan data for a patient in a reconstruction as shown in FIG. 7. As another example, acts for gathering and/or accessing training data are performed.

In act 600, a computer (e.g., image processor) machine trains a model for reconstruction, such as training for a neural network for regularization. To machine train, training data is gathered or accessed. The training data includes many sets of data, such as image or object domain data. Tens, hundreds, or thousands of sample image data from reconstruction are acquired, such as from scans of patients, scans of phantoms, simulation of scanning, and/or by image processing to create further samples. Many examples that may result from different scan settings, patient anatomy, scanner characteristics, or other variance that results in different samples in scanning are used. In one embodiment, the samples are for MR compressed sensing, such as image domain data resulting from under sampled k-space data. The samples may be for many different applications and/or types of imaging, resulting in a larger set of training data. The training uses multiple samples of input sets, such as object domain data representing patients after Fourier transform and/or gradient calculation. The samples are used in deep learning to determine the values of the learnable variables (e.g., values for convolution kernels) that produce outputs with minimized cost function and/or maximized likelihood of being a good representation (i.e., discriminator cannot tell the difference) across the variance of the different samples.

The training data may and/or may not include ground truth information. The desired representation or image resulting from a given sample is and/or is not provided. For example, the image data without or with reduced artifacts to be output by regularization is provided as ground truth with some or all of the samples of input image data.

Deep learning is used to train the model. The training learns both the features of the input data and the conversion of those features to the desired output (i.e., denoised or regularized image domain data). Backpropagation, RMSprop, ADAM, or another optimization is used in learning the values of the learnable parameters of the regularization 224 (i.e., the CNN). Where the training is supervised, the differences (e.g., L1, L2, or mean square error) between the estimated output and the ground truth output are minimized. Where a discriminator is used in training, the ground truth is not needed. Instead, the discriminator determines whether the output is real or estimated as an objective function for feedback in the optimization. The characteristic is one that likely distinguishes between good and bad output by examining the output rather than by comparison to a known output for that sample. Joint training (e.g., semi-supervised) may be used.

Any hierarchal and/or iterative architecture or layer structure for machine learning to regularize in reconstruction may be used. The architecture defines the structure, learnable parameters, and relationships between parameters. In one embodiment, a convolutional or another neural network is used for the regularizer. Deep machine training is performed. Any number of hidden layers may be provided between the input layer and output layer.

In one embodiment, the architecture includes a sequence of iterations or unrolled iteration networks. A neural network with an unrolled arrangement of U-blocks in a sequence is machine trained as a regularizer for the reconstruction in the medical imaging. The architecture may include U-blocks with down-sampling and up-sampling, such as implemented as a CNN, fully connected network, or another network arrangement. In additional or alternative embodiments, the architecture includes one or more hierarchal U-networks, such as one or more (e.g., each) of the U-blocks for iteration including hierarchal U-networks. The hierarchal U-networks have blocks at different scales with down and up-sampling, providing down and up-sampling in at least one block that is part of a down-sampling chain and/or providing down and up-sampling in at least one block that is part of an up-sampling chain. The iterative and/or hierarchal architecture is machine trained, such as machine training with each of the U-blocks in the sequence having a hierarchy of U-networks. The U-networks may have local and/or global residual connections for data consistency.

In one embodiment, the machine-learned model 300 of FIGS. 3-5 is the architecture being trained. The CNN is machine trained. The feature extraction block 302, hierarchal U-blocks 304, memory block 306, and enhancement block 310 form a convolution network, which is machine trained. The hierarchal U-blocks 304 are trained as a sequence or unrolled configuration. The memory block 306 is trained to have the same weights or one memory block 306 is trained for application to outputs of the iterative hierarchal U-blocks 304. The memory block 306 is trained to receive outputs from the hierarchal U-blocks 304 of the sequence and separately process the outputs with shared weights.

Once trained, the neural networks are applied in reconstruction of a representation or image of a patient from a scan of that patient. For example, the machine-learned networks for regularization are used with reconstruction algorithms (e.g., gradient descent and extrapolation) during unrolled iterative reconstruction.

In one embodiment, the unrolled reconstruction is used. The unrolled reconstruction includes a set number of iterations, but another optimization stop criterion may be used. Each iteration may be handled differently. For example, a separate neural network or machine-learned model 300 is trained for each reconstruction iteration. The same or different architecture of the network is used for the different iterations. For example, different networks of the same architecture but with one or more different learned values of the learnable parameters are provided for different ones of the reconstruction iterations. In training, each network and weight or weights are trained simultaneously or together across iterations. By reconstructing as part of training, the simultaneous training for the different iterations is provided.

In another embodiment, the reconstruction or part of the reconstruction is an iterative optimization (i.e., not unrolled). The reconstruction includes an optimization. The machine-learned model (e.g., learned regularization network) is used within or as part of the reconstruction optimization, such as for denoising data.

After training, the machine-learned model or models are represented as a matrix, filter kernels, and/or architecture with the learned values. The learned convolution kernels, weights, connections, and/or layers of the neural network or networks are provided.

In act 620 of FIG. 6, the computer or image processor stores the machine-learned model resulting from the machine learning. For example, the regularizer network or networks, including the iteration order or sequence, are stored. The matrix or other parameterization of the machine-learned networks are saved in memory. The machine-learned model may be stored locally or transferred over a network or by moving the memory to other computers, workstations, and/or MR scanners.

The model resulting from the machine training using the plurality of the samples is stored. This stored model has fixed weights or values of learnable parameters determined based on the machine training. These weights or values are not altered by patient-to-patient or over multiple uses for different medical scans. The weights or values are fixed, at least over a number of uses and/or patients. The same weights or values are used for different sets of scan data corresponding to different patients. The same values or weights may be used by different medical scanners. The fixed machine-learned model or models are to be applied without needing to train as part of the application. Re-training or updated training may be provided.

Once trained, the machine-learned model (e.g., learned CNN) is used for reconstruction of a spatial representation from input k-space measurements for a patient. For example, the machine-learned model is applied for regularization in the reconstruction.

FIG. 7 is a flow chart diagram of one embodiment of a method for reconstruction of a medical image in a medical imaging system, such as reconstruction of a MR image in an MR system. A machine-learned model as trained is applied for regularization in the reconstruction of an image for a patient. The machine-learned model was previously trained and includes a hierarchal and/or iterative network.

The application is part of scanning for patient diagnosis. The scan is performed as one of different imaging applications for different anatomy and/or disease. Due to versatility of the hierarchal and/or iterative network in regularization, the same machine-learned model may be applied to different imaging applications, such as for different anatomy and/or disease. The machine-learned network is applied independent of the different imaging applications. The machine-learned network may have been trained on reconstructions or regularization for the different imaging applications.

The method is performed by the system of FIG. 1 or another system. The medical scanner scans the patient. An image processor reconstructs the image using the machine-trained model, and a display displays the medical image. Other components may be used, such as a remote server or a workstation performing the reconstruction and/or display.

The method is performed in the order shown or other orders. Additional, different, or fewer acts may be provided. For example, a preset, default, or user input settings are used to configure the scanning prior art act 700. As another example, the image is stored in a memory (e.g., computerized patient medical record) or transmitted over a computer network instead of or in addition to the display of act 730. In another example, one or more of acts 722, 724, and/or 726 are not performed as these acts represent one embodiment or example of performing act 720.

In act 700, the medical system scans a patient. For example, an MR scanner or another MR system scans the patient with an MR compressed (e.g., under sampling), parallel, compressed parallel, or another MR sequence. The amount of under sampling is based on the settings, such as the acceleration. Based on the configuration of the MR scanner, a pulse sequence is created. The pulse sequence is transmitted from coils into the patient. The resulting responses are measured by receiving radio frequency signals at the same or different coils. The scanning results in k-space measurements as the scan data.

In another example, a computed tomography scanner scans a patient by transmitting x-rays from different angles through the patient. The scanning results in detected projections for a given patent as the scan data.

In act 720, an image processor reconstructs a representation of the patient from the scan data. For MR reconstruction, the k-space data is Fourier transformed into scalar values representing different spatial locations, such as spatial locations representing a plane through or volume of a region in the patient. Scalar pixel or voxel values are reconstructed as the MR image. The spatial distribution of measurements in object or image space is formed. This spatial distribution represents the patient.

The reconstruction is performed, at least in part, using a deep machine-learned model, such as a neural network trained with deep machine learning, for regularization. The machine-learned model is previously trained, and then used in reconstruction as trained. Fixed values of learned parameters are used for application. In application of the already trained network, the reconstruction process is followed. The machine-learned model is used in the reconstruction. For example, regularization is performed in every or only some iterations using the deep learned network (e.g., CNN of FIGS. 3-5). In response to the input for a given patient, a patient specific image is reconstructed. The machine-learned model outputs the image as pixels, voxels, and/or a display formatted image in response to the input. The learned values and network architecture, with any algorithms (e.g., extrapolation and gradient update) determine the output from the input.

The output of the machine-learned network is a two-dimensional distribution of pixels representing an area of the patient and/or a three-dimensional distribution of voxels representing a volume of the patient. The output from the last reconstruction iteration may be used as the output representation of the patient.

The machine-learned network of the machine-learned model implements a regularizer. The reconstruction is performed iteratively with gradients, a Fourier transform, and the regularizer. The regularizer receives image space information from the Fourier transform or after the gradient operation and outputs denoised image space information.

The reconstruction may be iterative. Each iteration determines an updated image object from an input image object, with the gradient operation comparing fit with the measurements. For example, an unrolled iterative reconstruction is performed. Different machine-learned networks are used for the different iterations. Some iterations may not include regularization, and at least one iteration does include a machine-learned model for regularization. For example, an initial sequence of iterations does not include regularization, and a subsequent sequence of iterations includes regularization with machine learned models. After the last iteration, the output representation by the regularizer or gradient update is provided for imaging or the medical record of the patient.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image as a further display image. In alternative embodiments, the machine-learned network outputs the display image directly in response to the input.

Acts 722, 724, and 726 represent one embodiment of the reconstruction with the machine-learned regularizer of act 720. In the reconstruction, a regularizer for at least one reconstruction iteration is implemented with a machine-learned network. Additional, different, or fewer acts may be provided.

In act 722, a complex image output by a gradient update, Fourier transform, or other reconstruction operation is received. A computer or image processor receives the pixels, voxels, or other data in object or image space. In alternative embodiments, image data that is not complex is received.

In act 724, the image processor or computer applies a machine-learned hierarchal and/or iterative regularizer. The received complex image data is input to the input channels of the machine-learned model.

In one embodiment, the machine-learned network of FIG. 3 is applied. The machine-learned network includes a feature extraction block of one or more convolution layers. The feature extraction block is prior to the iterative convolutional networks, so forms the input channels. The complex image with real and imaginary values is input to two channel inputs.

The machine-learned network may be iterative, such as providing iterative hierarchal convolutional networks. Each of the iterative hierarchal convolutional networks may include both down-sampling and up-sampling. This unrolled network structure provides a series of CNNs, which may have different weights and the same architecture.

The machine-learned network may be hierarchal. For example, the iterative CNNs each have U-blocks at different levels of the down-sampling and the up-sampling chains, such as shown in FIG. 4. None, one, or more (e.g., at least one) concatenation connection may be provided in parallel with a bottleneck. The U-blocks themselves also include down-sampling and up-sampling layers, so that down and up-sampling is provided in one block of a down-sampling or up-sampling chain (e.g., nested). The U-blocks may include local and/or global connections.

The machine-learned network may include other structure. For example, a memory network with convolution layers is applied separately to the outputs of the iterative convolutional networks. The outputs from the memory network are concatenated and input to an enhancement block of one or more convolutional layers. The enhancement block receives a concatenation of outputs of the memory network and outputs the medical image as regularized in act 726. The output medical image may be further processed, such as further reconstruction iterations. The output medical image for the last reconstruction iteration may be further processed, such as filtering, rendering or color mapping. The output medical image may have complex values or real values.

In act 730, a display (e.g., display screen) displays the medical image, such as the MR image. The medical image, after or as part of any post processing, is formatted for display on the display. The display presents the image for viewing by the user, radiologist, physician, clinician, and/or patient. The image assists in diagnosis.

The displayed image may represent a planar region or area in the patient. Alternatively or additionally, the displayed image is a volume or surface rendering from voxels (three-dimensional distribution) to the two-dimensional display.

The same deep machine-learned model may be used for different patients. The same or different copies of the same machine-learned model are applied for different patients, resulting in reconstruction of patient-specific representations or reconstructions using the same values or weights of the learned parameters of the model. Different patients and/or the same patient at a different time may be scanned while the same or fixed trained machine-learned regularization model is used in reconstruction the image. Other copies of the same deep machine-learned model may be used for other patients with the same or different scan settings and corresponding sampling or under sampling in k-space.

Although the subject matter has been described in terms of exemplary embodiments, it is not limited thereto. Rather, the appended claims should be construed broadly, to include other variants and embodiments, which can be made by those skilled in the art.

What is claimed is:

1. A method for reconstruction of a medical image in a medical imaging system, the method comprising:
    scanning, by the medical imaging system, a patient, the scanning resulting in measurements;
    reconstructing, by an image processor, the medical image from the measurements, the reconstructing including a regularizer implemented with a machine-learned network comprising iterative hierarchal convolutional networks, each of the iterative hierarchal convolutional networks including both down-sampling and up-sampling nested within other down-sampling and up-sampling; and
    displaying the medical image.

2. The method of claim 1 wherein scanning comprises scanning with the medical imaging system being a magnetic resonance (MR) scanner and the measurements being k-space measurements.

3. The method of claim 1 wherein reconstructing comprises reconstructing as an unrolled iterative reconstruction where each of multiple reconstructions in the unrolled iterative reconstruction includes regularization, the regularizer providing the regularization for at least one of the multiple reconstructions.

4. The method of claim 1 wherein reconstructing comprises reconstructing with the machine-learned network including a feature extraction block comprising one or more convolution layers, the feature extraction block being prior to the iterative hierarchal convolutional networks.

5. The method of claim 1 wherein reconstructing comprises reconstructing with the machine-learned network wherein the iterative hierarchal convolutional networks have different weights.

6. The method of claim 1 wherein reconstructing comprises reconstructing with the machine-learned network further comprising a memory network with convolution layers, the memory network applied separately to the outputs of the iterative hierarchal convolutional networks.

7. The method of claim 6 wherein reconstructing comprises reconstructing with the machine-learned network further comprising an enhancement block of one or more convolutional layers, the enhancement block receiving a concatenation of outputs of the memory network and outputting the medical image as regularized.

8. The method of claim 1 wherein reconstructing comprises receiving a complex image output by a gradient update, the machine-learned network having two channel input for the complex image, and outputting the medical image with complex values.

9. The method of claim 1 wherein reconstructing comprises reconstructing with the iterative hierarchal convolutional networks each comprising U-blocks at different levels of the down-sampling and the up-sampling and comprising at least one concatenation connection in parallel with a bottleneck.

10. The method of claim 9 wherein the U-blocks comprise down-sampling and up-sampling layers and comprise local and global connections.

11. The method of claim 1 wherein scanning comprise scanning for patient diagnosis as one of different imaging applications for different anatomy and/or disease, and wherein reconstructing comprises application of the machine-learned network independent of the different imaging applications, the machine-learned network having been trained on reconstructions for the different imaging applications.

12. A method of machine training for reconstruction in medical imaging, the method comprising:
    machine training a neural network with an unrolled arrangement of U-blocks in a sequence as a regularizer for the reconstruction in the medical imaging, the neural network comprising some of the U-blocks nested within other of the U-blocks; and
    storing the neural network as machine trained.

13. The method of claim 12 wherein machine training comprises machine training the neural network with the U-blocks comprising convolutional neural networks with down-sampling and up-sampling.

14. The method of claim 12 wherein machine training comprises machine training with each of the U-blocks in the sequence having a hierarchy of U-networks.

15. The method of claim 14 wherein machine training comprises machine training with the hierarchy of U-networks, each of the U-networks in the hierarchy having local and global residual connections.

16. The method of claim 12 wherein machine training comprises machine training the neural network with the neural network further comprising a convolution network configured to receive outputs from the U-blocks of the sequence and separately process the outputs with shared weights.

17. The method of claim 12 wherein machine training comprises machine training with ground truth imaging from different medical applications and/or types of imaging.

18. A system for reconstruction in medical imaging, the system comprising:
    a medical scanner configured to scan a region of a patient, the scan providing scan data;
    an image processor configured to reconstruct a representation of the region from the scan data, the image processor configured to reconstruct by application of a machine-learned model in a regularization stage, the machine-learned model comprising a down-sampling and up-sampling first block having multiple down-sampling and up-sampling second blocks; and
    a display configured to display an image of the region from the reconstructed representation.

19. The system of claim 18 wherein the down-sampling and up-sampling first block is one of a sequence of down-sampling and up-sampling first blocks in the regularization stage.

20. The system of claim 18 wherein the down-sampling and up-sampling first block comprises a first convolutional neural network, and wherein the down-sampling and up-sampling second blocks comprise second convolutional neural networks.

* * * * *